(12) United States Patent
Winter (10) Patent No.: US 9,370,344 B2
(45) Date of Patent: Jun. 21, 2016

(54) METHOD OF FUSING LAYERS OF BIOLOGICAL TISSUE

(75) Inventor: Hanno Winter, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 887 days.

(21) Appl. No.: 13/260,847

(22) PCT Filed: Apr. 29, 2010

(86) PCT No.: PCT/EP2010/055814
§ 371 (c)(1),
(2), (4) Date: Sep. 28, 2011

(87) PCT Pub. No.: WO2010/125146
PCT Pub. Date: Nov. 4, 2010

(65) Prior Publication Data
US 2012/0022531 A1    Jan. 26, 2012

Related U.S. Application Data

(60) Provisional application No. 61/217,607, filed on Jun. 1, 2009.

(30) Foreign Application Priority Data

Apr. 30, 2009   (DE) .................. 10 2009 002 768

(51) Int. Cl.
*A61B 17/00* (2006.01)
*A61B 17/11* (2006.01)
(Continued)

(52) U.S. Cl.
CPC ........... *A61B 17/00491* (2013.01); *A61B 17/11* (2013.01); *A61L 31/14* (2013.01); *A61B 18/1206* (2013.01); *A61B 18/14* (2013.01); *A61B 2017/00504* (2013.01); *A61B 2018/00011* (2013.01); *A61B 2018/00345* (2013.01);
(Continued)

(58) Field of Classification Search
CPC ............. A61B 17/00491; A61B 17/11; A61B 2017/00504; A61B 2018/00755; A61L 31/14
USPC ............................................ 606/51; 128/898
See application file for complete search history.

(56) References Cited

U.S. PATENT DOCUMENTS 5,603,711 A * 2/1997 Parins et al. .................... 606/51
5,810,808 A * 9/1998 Eggers ............................ 606/48
(Continued)

FOREIGN PATENT DOCUMENTS

DE         198 60 304 A1    6/2000
WO    WO 2008/125259 A1    10/2008

OTHER PUBLICATIONS

Lauto et al.; "Chitosan Adhesive for Laser Tissue Repair: In Vitro Characterization," *Lasers in Surgery and Medicine*; 2005; pp. 193-201; vol. 36; Wiley-Liss, Inc.
(Continued)

*Primary Examiner* — Christopher A Flory
(74) *Attorney, Agent, or Firm* — Oliff PLC (57) ABSTRACT

A biocompatible material layer for use as an intermediary layer between body tissue surfaces to be fused in a body tissue fusion, wherein the material layer includes two sides opposite to one another, wherein the material layer is configured so that it provides portions with comparatively higher electrical resistance and portions with comparatively lower electrical resistance between body tissue surfaces to be fused.

1 Claim, 8 Drawing Sheets

(51) Int. Cl.
    *A61L 31/14*   (2006.01)
    *A61B 18/12*   (2006.01)
    *A61B 18/14*   (2006.01)
    *A61B 18/00*   (2006.01)
(52) U.S. Cl.
    CPC ......... *A61B2018/00404* (2013.01); *A61B 2018/00619* (2013.01); *A61B 2018/00755* (2013.01); *A61B 2018/00875* (2013.01)

(56) References Cited

U.S. PATENT DOCUMENTS

| | | | | |
|---|---|---|---|---|
| 5,961,526 | A * | 10/1999 | Chu et al. | 606/113 |
| 6,066,134 | A * | 5/2000 | Eggers et al. | 606/32 |
| 6,655,386 | B1 * | 12/2003 | Makower et al. | 128/898 |
| 6,726,696 | B1 * | 4/2004 | Houser et al. | 606/151 |
| 7,169,146 | B2 * | 1/2007 | Truckai et al. | 606/41 |
| 7,354,440 | B2 * | 4/2008 | Truckai et al. | 606/51 |
| 7,534,243 | B1 * | 5/2009 | Chin et al. | 606/49 |
| 7,588,565 | B2 * | 9/2009 | Marchitto et al. | 606/27 |
| 7,967,839 | B2 * | 6/2011 | Flock et al. | 606/213 |
| 8,021,362 | B2 * | 9/2011 | Deem et al. | 606/41 |
| 8,038,673 | B2 * | 10/2011 | Malecki et al. | 606/41 |
| 8,057,469 | B2 * | 11/2011 | Deem et al. | 606/41 |
| 8,066,701 | B2 * | 11/2011 | Malecki et al. | 606/41 |
| 8,109,274 | B2 * | 2/2012 | Horne et al. | 128/898 |
| 8,585,753 | B2 * | 11/2013 | Scanlon et al. | 623/1.42 |
| 2003/0065341 | A1 | 4/2003 | Schulze | |
| 2003/0069571 | A1 | 4/2003 | Treat et al. | |
| 2003/0216732 | A1 * | 11/2003 | Truckai | A61B 18/14 606/49 |
| 2003/0236518 | A1 | 12/2003 | Marchitto et al. | |
| 2004/0059280 | A1 * | 3/2004 | Makower et al. | 604/8 |
| 2004/0199161 | A1 * | 10/2004 | Truckai et al. | 606/48 |
| 2004/0210282 | A1 * | 10/2004 | Flock et al. | 607/96 |
| 2004/0230185 | A1 * | 11/2004 | Malecki et al. | 606/2 |
| 2005/0021026 | A1 | 1/2005 | Baily | |
| 2005/0033277 | A1 * | 2/2005 | Clague | A61B 18/14 606/32 |
| 2005/0101904 | A1 * | 5/2005 | Wilk | 604/8 |
| 2005/0113936 | A1 * | 5/2005 | Brustad | A61B 17/06166 623/23.71 |
| 2007/0112347 | A1 * | 5/2007 | Malecki et al. | 606/41 |
| 2007/0123854 | A1 * | 5/2007 | Clague | A61B 18/14 606/45 |
| 2007/0167901 | A1 * | 7/2007 | Herrig et al. | 604/6.16 |
| 2007/0198034 | A1 * | 8/2007 | Ortiz et al. | 606/142 |
| 2007/0207186 | A1 * | 9/2007 | Scanlon et al. | 424/424 |
| 2007/0239260 | A1 | 10/2007 | Palanker et al. | |
| 2008/0140070 | A1 * | 6/2008 | Filloux et al. | 606/41 |
| 2008/0140113 | A1 * | 6/2008 | Taimisto et al. | 606/213 |
| 2008/0140170 | A1 * | 6/2008 | Filloux et al. | 607/122 |
| 2009/0182331 | A1 * | 7/2009 | D'Amelio | A61B 18/1442 606/51 |
| 2009/0299367 | A1 * | 12/2009 | Ginnebaugh et al. | 606/51 |
| 2010/0042092 | A1 * | 2/2010 | Marchitto et al. | 606/33 |
| 2011/0288369 | A1 * | 11/2011 | Ginnebaugh et al. | 600/36 |
| 2012/0233844 | A1 * | 9/2012 | Johnson | A61B 17/07207 29/428 |
| 2013/0226165 | A1 * | 8/2013 | Manwaring et al. | 606/30 |

OTHER PUBLICATIONS

Bregy et al.; "Electromagnetic Tissue Fusion Using Superparamagnetic Iron Oxide Nanoparticles: First Experience with Rabbit Aorta;" *The Open Surgery Journal*; 2009; pp. 3-9; vol. 2; Bentham Science Publishers Ltd.

International Search Report dated Jul. 30, 2010 in International Application No. PCT/EP2010/055814.

Written Opinion of the International Searching Authority dated Jul. 30, 2010 in International Application No. PCT/EP2010/055814.

* cited by examiner

METHOD OF FUSING LAYERS OF BIOLOGICAL TISSUE

The invention relates, on the one hand, to a biocompatible material layer for use as an intermediary layer between body tissue surfaces to be fused through body tissue fusion; on the other hand, the invention relates to an electrosurgical system for electrosurgical fusion of body tissue.

Electrosurgical fusion of body tissue is known in principle and described e.g. in US 2007/0239260 or WO 2008/125259. Additional descriptions can be found in Lauto et al., "Chitosan Adhesive for Laser Tissue Repair: In Vitro Characterization", Lasers in Surgery and Medicine, Bd. 36, pgs. 139-201, 2005, as well as in Bregyi et al., "Electromagnetic Tissue Fusion Using Superparamagnetic Iron Oxide Nanoparticles: First Experience with Rabbit Aorta", The open Surgery Journal, 2008, Bd. 2, pgs. 3-9.

Electrosurgical tissue fusion is used e.g. instead of conventional sutures. Optimum tissue closure is a significant requirement for a recovery without complications for a surgically treated patient. Studies prove that all essential prior post surgery complications after a minimal invasive surgical procedure result from impaired wound healing.

Through the development of impedance regulated bipolar high frequency technology, a cost effective and surgically established procedure for cutting, coagulating and thermal closure of blood vessels is provided. Depending on temperature, time and pressure, it is also possible to fuse other types of tissues than previously, e.g. intestinal walls, urethra or skin, in order to close wounds. For this purpose, a thermally induced transformation process (denaturation of the human proteins present in the tissue) can be used. However, it is a prerequisite for a successful wound closure through tissue heating that damages to the tissue cells through overheating are kept as small as possible and locally limited.

Fusing body tissue can be improved by an intermediary layer of fusion enhancing material like e.g. albumin. Using an intermediary layer for tissue fusion is already known from the two publications recited supra.

Thus, it is the object of the invention to facilitate an improved thermal tissue fusion.

This object is accomplished, on the one hand, through a biocompatible material layer of the type recited supra, which has two sides opposite to one another and is configured so that it creates portions of comparatively higher electrical resistance and portions of comparatively lower electrical resistance between the body tissue surfaces to be fused. This is preferably provided in that the material layer includes sections with different electrical resistance between the sides of the material layer opposing one another.

The material layer can be provided with such portions with different electrical resistances through making the material layer from a material that has a higher electrical resistance than fusing body tissue and in that the material layer has sections with different layer thickness. In an extreme case, the layer thickness can be zero, so that the material layer includes holes, which then cause portions with a comparatively lower electrical resistance.

Preferably, the material layer is made from a material that has an electrical resistance, which is e.g. at least five times as high as the resistance of non-coagulated body tissue. Depending on the material, the resistance during the fusion can be fixed or variable.

Alternatively or additionally, the material layer can also be made from different materials in sections, wherein the respective materials differ from one another through their specific electrical resistances, so that the material layer has a different electrical resistance in particular sections between opposite points of their opposite sides. Thus, the resistances of the various materials differ at least by a factor of 5.

The object of the invention is furthermore accomplished by an electrosurgical system for thermal tissue fusion, which comprises at least two electrodes for emitting or receiving electrical power, which flows through body tissue to be fused during operation. A component of the electrosurgical system is furthermore a material layer of the type described supra. The electrodes of the electrosurgical system are thus sized so that their respective surfaces effective for electrical power emission or electrical power reception are larger respectively than the surfaces of the respective portions provided by the material layer, which have a comparatively lower electrical resistance and which are effective during the tissue fusion. This way, it is assured that the electrical power introduced into the body tissue causes the greatest heating of the body tissue in the portion of the portions with comparatively lower electrical resistance, and thus not proximal to the electrodes.

It is an essential advantage of a material layer according to the invention that it facilitates to create portions of high electrical power density adjacent to portions with lower electrical power density. Since the portions with high power density are concentrated at the material layer, and thus not at the electrodes, this causes focused tissue fusion through tissue heating exactly at the cutting surface between the tissue layers to be fused.

The invention is based on the finding that an electrical current flowing through body tissue can cause three different effects, as a function of strength of current, type of current and frequency. Besides the electrolytic effect and the Faraday effect (nerve excitation), the thermal effect is particularly important for surgical applications. The Joule law states for an electrical conductor, like in this case the body tissue, that the heating of the electrical conductor is directly proportional to the square of the strength of the current and the electrical resistance of the conductor and indirectly proportional to the conductor cross section. This general relationship of converting the introduced electrical energy into thermal energy also applies to body tissue flowed through by electrical current under the provision of additional influencing factors. Through the invention described herein, it is possible to locally limit the heating of body tissue induced by electrical power, in particular high frequency AC power, so that the natural wound healing is only minimally disturbed and the strength of the tissue bond is not impaired, since between the body tissue portions, which are exposed to more heating in the portions of low electrical resistance, also such body tissue portions remain, which are heated less (in the portions of comparatively higher electrical resistance), and therefore do not denaturate, but can help with efficient wound healing.

As stated supra, this is caused by the material layer recited supra and the described electrosurgical system. The material layer provided as an intermediary layer for tissue fusion can be made of biological material, like e.g. collagen, albumin, fibrinogen, and chitin or similar. For tissue fusion, it is placed between the body tissues to be fused and can stay there.

The material layer can in particular also be entirely or partially made of bioresorbable and/or biodegradable material, like PGA, L-PLA (polylactid acid), PDS or PCL.

Thus, the intermediary layer can be solid, but it can also be configured as a gel or also a combination of both. It is essential that the intermediary layer causes portions with different levels of resistance. This has the effect that in particular portions with comparatively low electrical resistance are flowed through by current, when current is applied, while a lower power density is provided in the portion with comparatively higher electrical resistance. Based on the higher power density in the portions with lower electrical resistance, a higher heating of the body tissue is achieved in these portions than in the portions with higher electrical resistance.

With respect to the electrosurgical system, it is preferred in particular that the electrodes are components of an electrosurgical instrument, which is configured to grip body tissue to be fused with a material layer disposed there between, and to preferably clamp it between the electrodes. Preferably, the electrodes are disposed for this purpose at a distal end of the electrosurgical instrument.

It is particularly advantageous when the electrosurgical instrument is configured, so that the electrodes can be cooled during operation. This helps to avoid reliably that a strong heating of the body tissue occurs proximal to the electrodes, and thus an undesirable denaturation. A respective cooling can be e.g. a fluid cooling. For this purpose, respective cooling channels can be provided in the portion of the electrodes.

According to an embodiment, the electrodes are configured as free ends of the electrosurgical instrument, which can be moved like pincers or scissors.

The movable free ends of the electrosurgical instrument are preferably movable through parallel kinematics, which assure that the electrodes disposed opposite to one another at the free ends of the electrosurgical instrument move parallel towards one another when the electrosurgical instrument is actuated accordingly.

According to an alternative embodiment, the electrodes are movable relative to one another in longitudinal direction of the electrosurgical instrument. Thus, preferably an electrode disposed the furthest distal at the electrosurgical instrument is removably connected with a tension element at the distal end of a shaft of the electrosurgical instrument. Such an electrosurgical instrument can furthermore be configured similar to a known circular stapler.

It is advantageous in particular when the electrosurgical instrument is configured so that the clamping force imparted by the electrodes at the distal end of the electrosurgical instrument during application upon tissue disposed there between, thus the pressure in the tissue, can be pre-adjusted. It is advantageous in particular when the electrosurgical instrument is furthermore configured so that it generates a predetermined profile of the clamping force and thus of the pressure in the tissue, self-acting during tissue fusion. Thus, the electrosurgical instrument can be configured so that the clamping force imparted by the electrodes upon the tissue, and thus the pressure in the tissue, increases during tissue fusion.

Furthermore, the electrosurgical instrument, possibly in combination with a generator, which can be connected or is connected, can be configured so that it detects process parameters prevailing during tissue fusion, like e.g. impedance between electrodes, tissue temperature, clamping force or similar, and according to another embodiment so that it causes an automatic cutoff or regulation of the tissue fusion as a function of one or plural of these parameters.

The invention shall now be illustrated in more detail with reference to preferred embodiments and drawing figures, wherein.

Figure 1A:
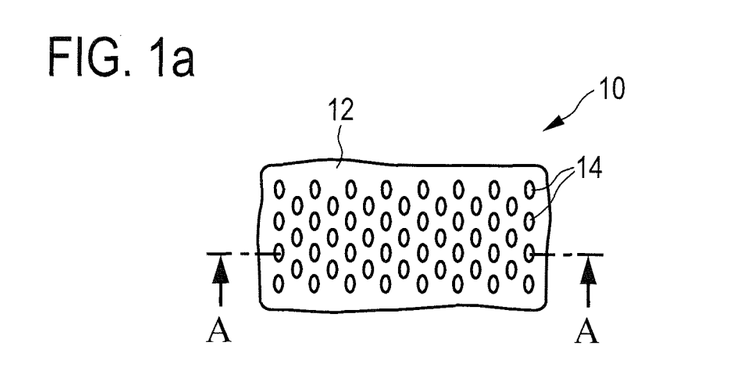
FIGS. 1a-1d illustrate an intermediary layer according to the invention in a top view and in a longitudinal sectional view.
Figure 1B:
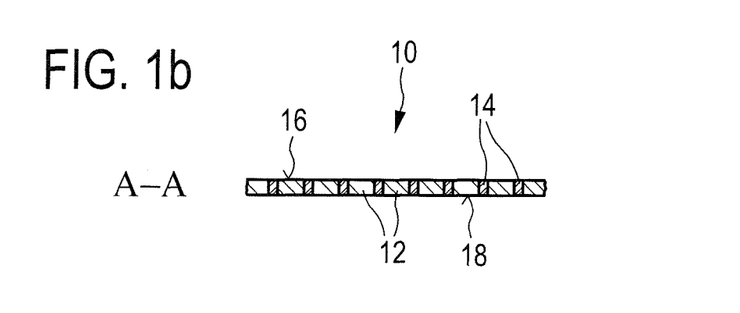

The material layer 10 illustrated in FIG. 1a in top view and in FIG. 1b in a longitudinal sectional view has sections with different electrical resistance. The material layer is made of a biocompatible material with a specific electrical resistance, which is higher than the resistance of body tissue with blood circulation. The material layer 10 has a first cohesive portion 12 with a comparatively high electrical resistance, in which a plurality of second portions 14 with comparatively low electrical resistance is disposed. These portions 14 with low electrical resistance can be made e.g. from the same material like the first portion 12 with comparatively higher electrical resistance, with the prerequisite that the layer thickness of the material layer 10 in the area of the portions 14 with comparatively lower electrical resistance is less than the layer thickness 12 with comparatively high electrical resistance. The layer thickness in the portions 14 with comparatively low electrical resistance can be zero, so that the portions 14 with comparatively low electrical resistance are de facto holes in the material layer 10, which pass through the first portion 14 with comparatively high electrical resistance.

Figures 1C, 1D:
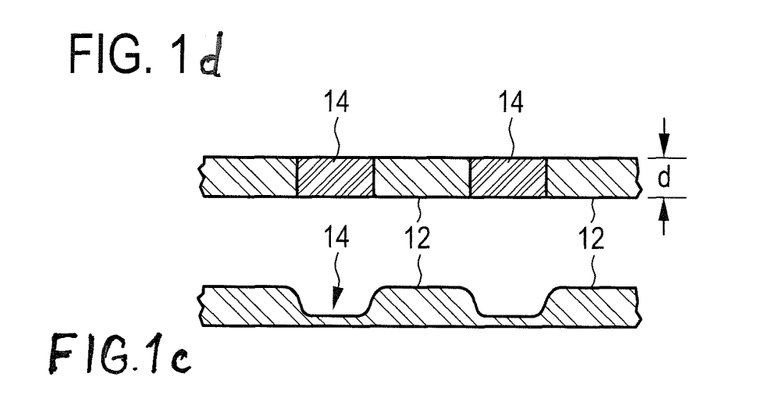

FIG. 1c illustrates how the thickness of the material layer 10 can be reduced in the portions 14 compared to the portion 12 in order to provide a lower electrical resistance. FIG. 1d illustrates that the material layer can also have a uniform thickness and can thus be made of materials with different specific electrical resistance 12, 14. Both measures can also be combined with one another.

According to an alternative embodiment, the portion 12 can also be the portion of the material layer 10, which causes a lower electrical resistance, while the portions 14 cause a comparatively high electrical resistance, because the material layer in these portions has a greater layer thickness or is made of a less conductive material.

As can be derived from the longitudinal sectional view in FIG. 1b, the material layer 10 is flat and therefore has two rather large surface sides 16 and 18, which are respectively oriented towards the tissue surfaces to be fused with one another during a tissue fusion.

The maximum layer thickness of the material layer 10 is preferably between 10 μm and 50 μm.

Figure 2:
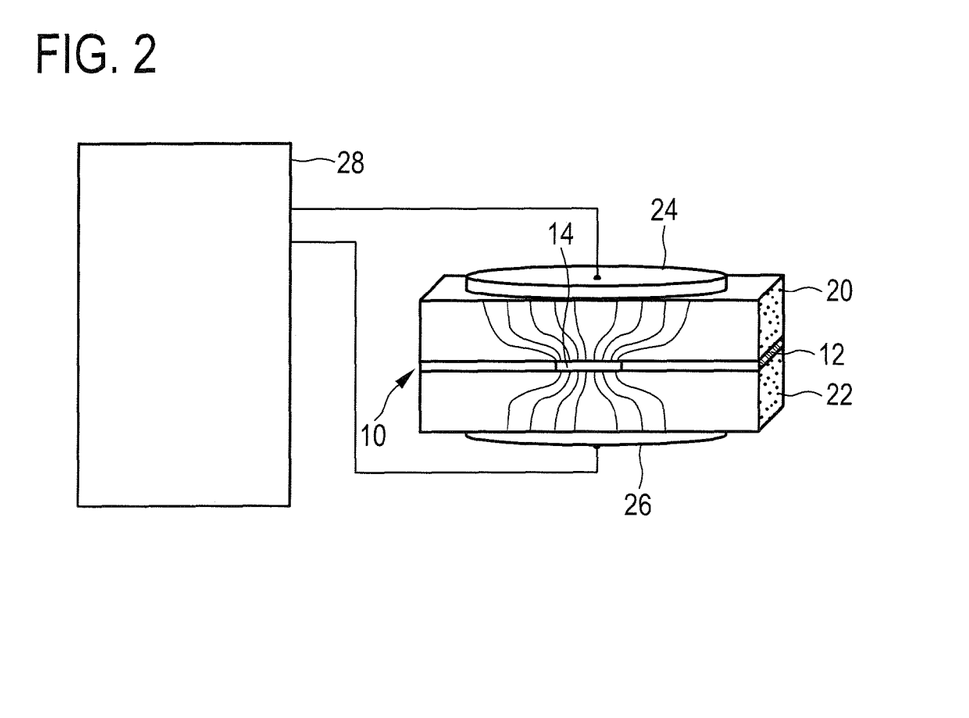
FIG. 2 illustrates a sketch depicting the basic principle of the invention.

FIG. 2 illustrates this with reference to a schematic sketch illustrating the basic principle of the invention. The sketch illustrates an electrosurgical system with a material layer 10 and electrodes 24 and 26 of a bipolar electrosurgical instrument, which need to be connected to a generator 28. It is illustrated how the material layer 10 is disposed during a tissue fusion between a first body tissue layer 20 in a second body tissue layer 22. The first body tissue layer 20 and the second body tissue layer 22 are contacted respectively by the first electrode 24 or by the second electrode 26 of an electrosurgical instrument, which is not illustrated in more detail. The electrodes 24 and 26 are connected to the generator 28. The generator 28 generates high frequency AC power during operation, which is passed through the two electrodes 24 and 26 and passed to the body tissues 20 and 22.

As can be derived from FIG. 2, the material layer 10 is illustrated so that only a single second portion 14 with comparatively low electrical resistance is illustrated, which is surrounded by the first portion 12 with comparatively higher electrical resistance. As schematically illustrated by FIG. 2, the second portion 14 with comparatively lower electrical resistance has the effect that the current flow is concentrated between the two electrodes 24 and 26 in the second portion 14 with a comparatively lower electrical resistance and the body tissue of the first and second body tissue layer 20 and 22 adjacent thereto. Put differently, in the area of the second portions 14 with comparatively lower electrical resistance, high power densities also prevail in the adjacent body tissue, which lead to a higher heating of the body tissue layers 20 and 22 in this portion, than in the adjacent body tissue sections, which are adjacent to the first portion 12 of the material layer 10 with comparatively higher electrical resistance.

FIG. 2 also illustrates that the entire surface of the respective electrodes 16 or 18 is greater than the entire surface of the second portions 12 of the material layer 10, so that no concentration of the power density and no undesired tissue heating occurs proximal to the electrodes.

Figure 3:
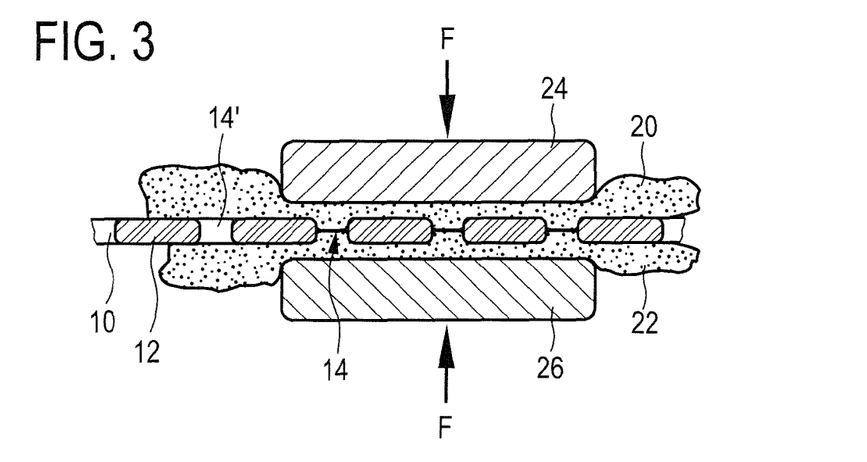
FIG. 3 illustrates another sketch depicting the basic principle of the invention.

In order to describe the basic principle of the invention in more detail, FIG. 3 in turn shows two body tissue layers 20 and 22 to be fused together with a material layer 10 according to the invention disposed between them. For the embodiment illustrated in FIG. 3, the second portions 14 with comparatively low electrical resistance are formed by holes in the material layer 10, which are surrounded by a cohesive first portion 12 with a compartitively higher electrical resistance.

FIG. 3 also illustrates two electrodes 24 and 26 for introducing high frequency AC power into the body tissue layers 20 and 22. FIG. 3 illustrates in particular that the electrodes 24 and 26 are preferably pressed onto one another during body tissue fusion and clamp the material layer 10 disposed there between according to the invention between one another. The clamping force F thus imparted by the electrodes 24 and 26 also has the effect that the two body tissue layers 20 and 22 contact one another in the second portions with comparatively low electrical resistance formed by the holes in the material layer 10. As a result, this means that the two body tissue layers to be fused contact one another in several portions defined by the second portions 14 of the material layer 10 according to the invention, while the material layer 10 provides a comparatively higher electrical resistance in other sections formed by the coherent first portion 12 with comparatively higher electrical resistance of the material layer 10. This has the effect that stronger body heating occurs as described with reference to FIG. 2, where the body tissue layers 20 and 22 to be fused contact one another in the portion of the second sections 14 of the material layer 10, because they are pressed into the holes 14 of the material layer 10 through the clamping force imparted by the electrodes. In these portions, a thermal welding of the two body tissue layers 20 and 22 occurs. These body tissue layers welded together are respectively surrounded by body tissue, which is heated less during the fusion, which body tissue is therefore not completely denaturized and can thus contribute to good wound healing.

A suitable clamping force for the force imparted by the electrodes 16 and 18 upon the body tissue layers 20 and 22 and the material layer 10 disposed there between is sized, so that it causes a pressure between 0.5 to 1.5 N/mm2. The electrosurgical instrument is preferably configured, so that the clamping force is adjustable. It is advantageous in particular when the electrosurgical instrument facilitates that a clamping force profile can be predetermined during a tissue fusion, which clamping force profile is then implemented self-acting by the electrosurgical instrument.

The electrodes 16 and 18 of an electrosurgical instrument suitable for the invention are preferably disposed at its respective distal end. Thus, the electrodes 16 and 18 are preferably movable relative to one another, so that body tissue layers to be fused and a material layer disposed there between can be clamped respectively between the electrodes 16 and 18.

In order to move the electrodes 16 and 18, differently than indicated in the figure, parallel kinematics are provided, which facilitate that the electrodes 16 and 18 always approach in parallel towards one another and this way impart a pressure through the electrode surface upon the tissue clamped between them that is as uniform as possible.

The surface area of the electrodes 16 and 18 effective for current conduction is sized relative to the material layer 10, so that it is greater than the entire surface of the portions 14, which cause a comparatively lower electrical resistance. Among this total surface area, the portions 14' must not be counted, which actually do not become effective during a tissue fusion, since they are not disposed in the tissue portion clamped between the electrodes 16 and 18.

Figure 4:
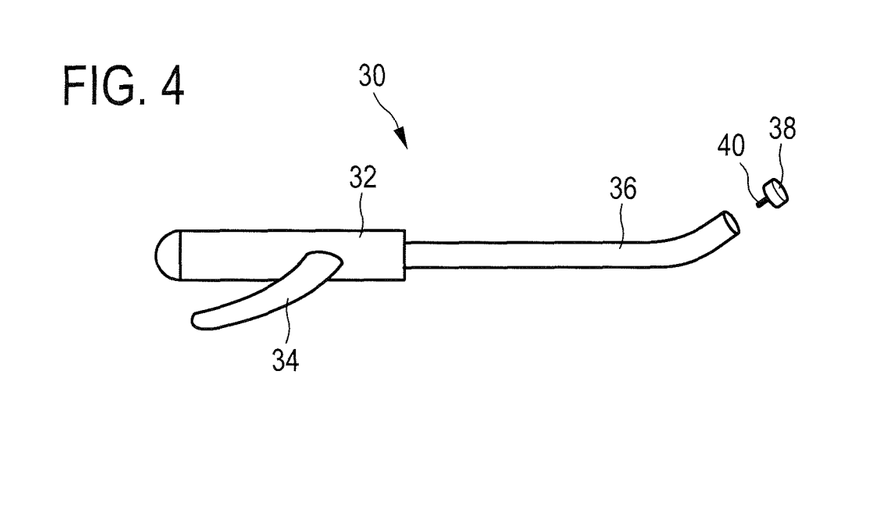
FIG. 4 illustrates an overview of the electrosurgical instrument.

FIG. 4 illustrates an exemplary electrosurgical instrument 30, which has a handle 32 with a lever 34 at the proximal end. A shaft 36 connects at the handle 32 at whose distal end a first annular electrode 16 is exposed. The second electrode 18 (opposite electrode) is a component of a counter piece 38, which can be disengaged from the electrosurgical instrument 30. The counter piece 38 can be coupled through a clutch pin 40 indicated in FIG. 4 with a pull element in the interior of the shaft 36, which is not shown in more detail in FIG. 4. An actuation of the handle 34 has the effect that the pull element imparts a pull force upon the clutch pin 40 of the counter piece 38 and thus presses the counter piece 38 and its annular electrode 18 in the direction towards the distal end of the shaft 38 and towards the annular electrode 16 disposed at this location. The counter piece thus becomes a thrust bearing for generating the clamping force.

Figure 5:
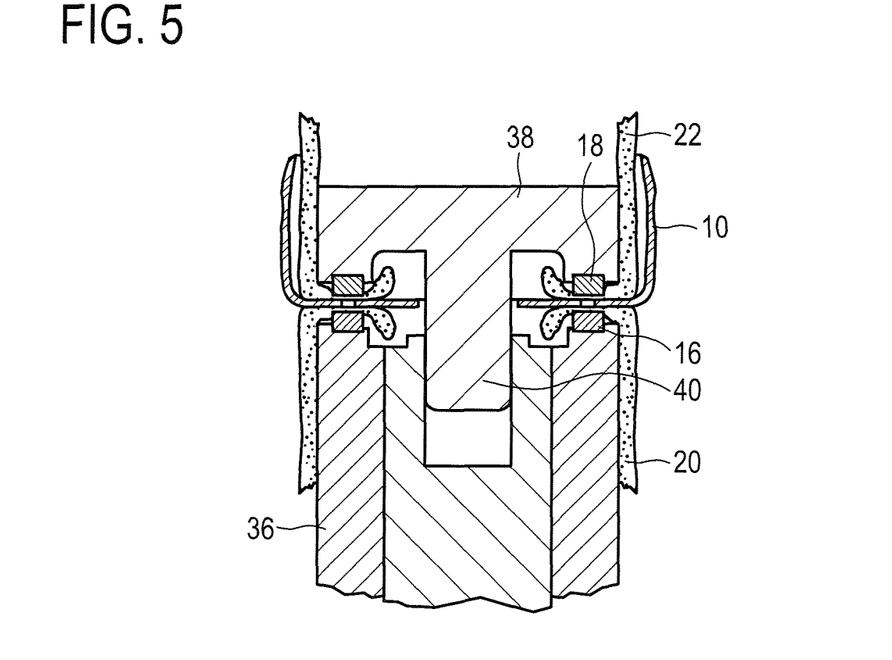
FIG. 5 illustrates a detail view of a distal end of the electrosurgical instrument of FIG. 4 in a longitudinal cut view.

FIG. 5 schematically illustrates an incomplete longitudinal sectional view of the distal end of the shaft 36 and the annular electrode 16 disposed at its face end of the counter piece 38 with its clutch pin 40 and of the also annular electrode 18 of the counter piece 38 opposite to the annular electrode 16 in the illustrated and coupled state. It is appreciated that FIG. 5 does not show the pull element disposed in the interior of the shaft 36 and the details of the coupling between this pull element and the coupling pin 40.

FIGS. 6a-6d illustrate how the electrosurgical instrument 30 of FIGS. 4 and 5 can be used together with a material layer according to the invention for connecting two sections of a hollow organ through end to end anastomosis through tissue fusion.

Figures 6A, 6B:
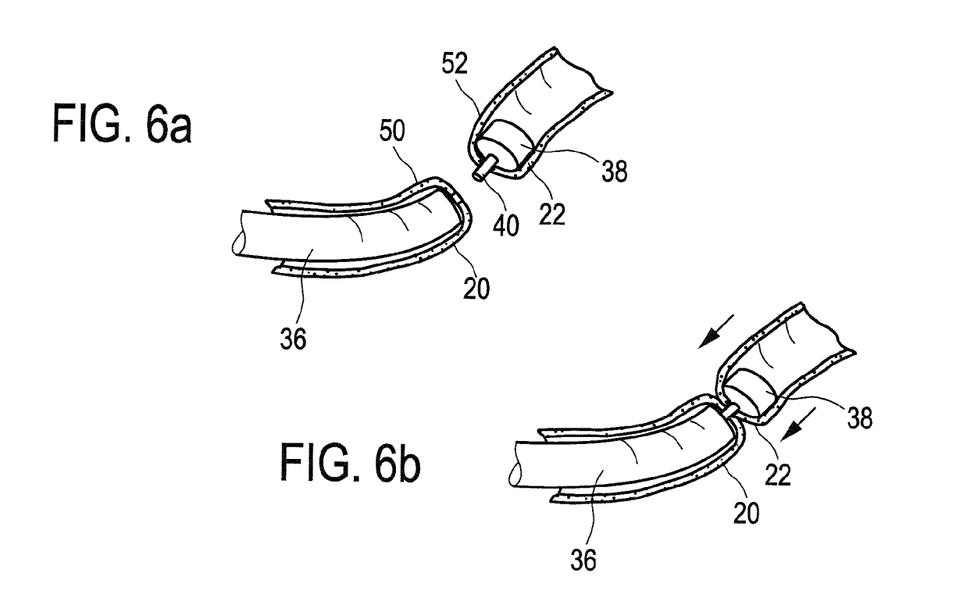
FIGS. 6a-6d illustrate sketches depicting the function of the electrosurgical instrument of FIGS. 4 and 5.

FIG. 6 initially illustrates schematically how the shaft 36 is inserted into a first end 50 of the hollow organ to be connected, while the counter piece 38 is inserted into a second end of the hollow organ to be connected. The body tissue forming the walls of the hollow organ to be connected thus forms the two body tissue layers to be clamped between the electrodes 16 and 18. As can be derived from FIG. 6a, the intestinal ends to be connected are reefed with a suture like in a purse-string suture, so that the body tissue layers to be fused are disposed in front of the electrode 16 or the electrode 18.

Figure 6C:
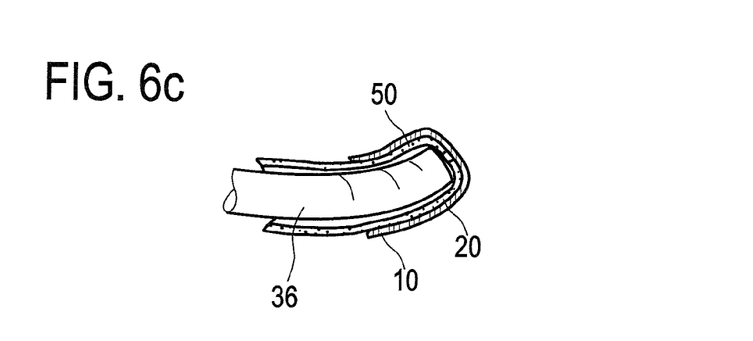
Figure 6D:
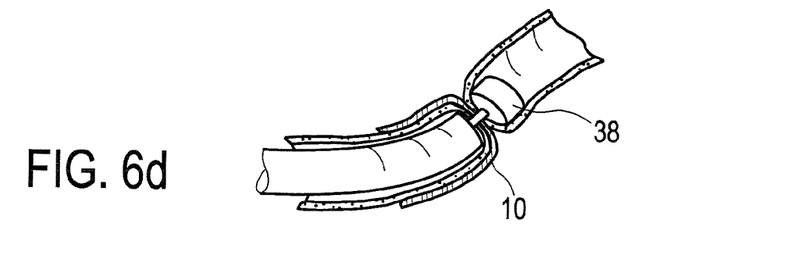

For tissue fusion, the counter piece 38 is then coupled with the pull element, which is not shown, in the shaft 36 of the electrosurgical instrument 30, and is subsequently pulled by means of the handle 32 against the distal end of the shaft 36. This is illustrated in FIG. 6d.

FIGS. 6a and 6b illustrate a body tissue fusion of a hollow organ without using the material layer according to the invention. FIG. 6c illustrates how the material layer 10 according to the invention can be placed over an end 50 of the hollow organ to be fused, before the shaft 36 of the electrosurgical instrument 30 is coupled with the counter piece 38. As a result, the material layer 10 is disposed between the body tissue layers to be fused as illustrated in FIG. 6b, as can be derived also from FIG. 5 in a detailed illustration.

Figure 7A:
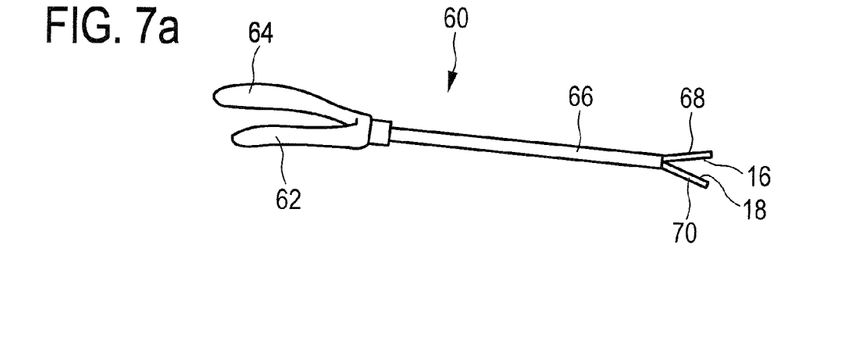
FIGS. 7a-7d illustrate components of a surgical system according to the invention in single view and also in applications.
Figure 7B:
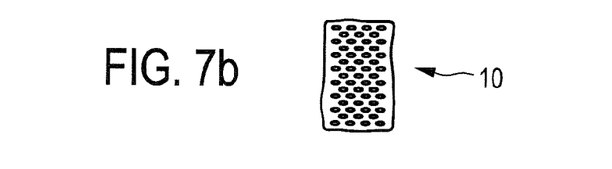
Figure 7C:
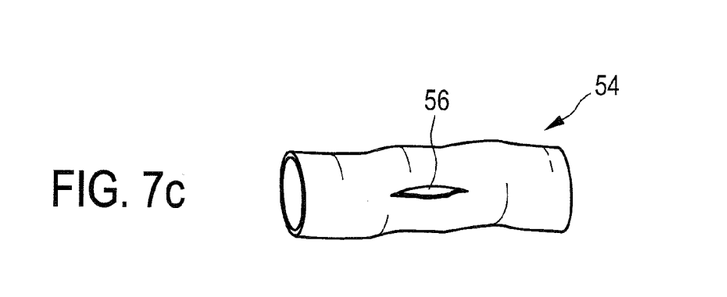
Figure 7D:
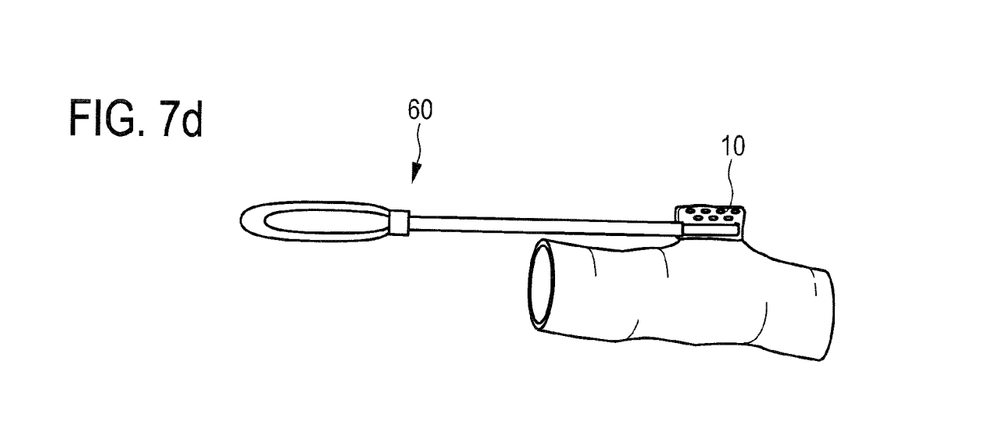
Figure 8A:
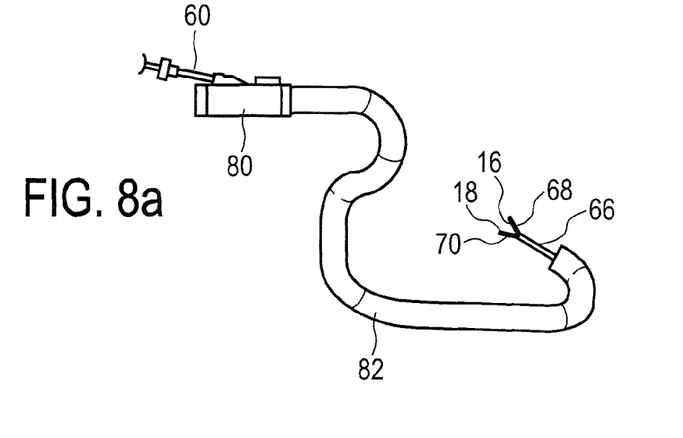
FIGS. 8a-8d illustrate an alternative electrosurgical system and its application.
Figure 8B:
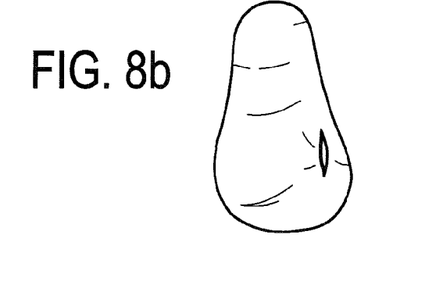
Figure 8C:
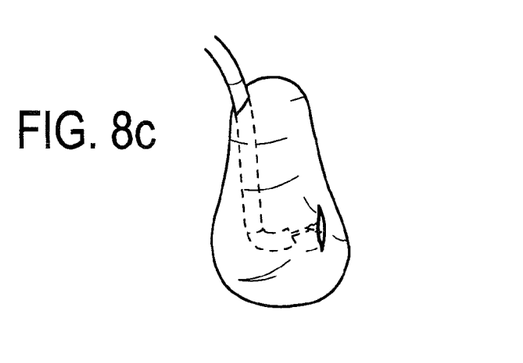
Figure 8D:
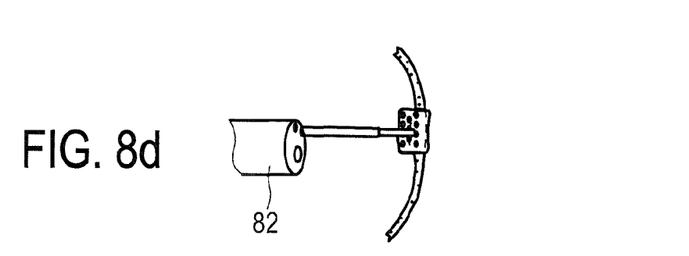

FIGS. 7a-7d illustrate an alternative electrosurgical instrument 60, which can be used in combination with an intermediary layer 10 according to the invention for treating incisions in a hollow organ, like e.g. an intestine. Thus, FIG. 7a illustrates the alternative electrosurgical instrument 60 and FIG. 7b illustrates the material layer 10 for use with the alternative electrosurgical instrument 60. The electrosurgical instrument 60 is a bipolar long shaft instrument with a shaft diameter of 5 mm. FIG. 7c illustrates a hollow organ 54 with an incision 56 to be treated with reference to an exemplary intestine. FIG. 7d eventually describes the treatment.

As can be derived from FIG. 7a, the electrosurgical instrument 60 on the side of the physician is configured at its proximal end similar to the electrosurgical instrument 30 of FIG. 4. Also, the electrosurgical instrument 60 has a handle 62 with an actuation lever 64 disposed thereon. A shaft 66 connects to the handle 62, at whose distal end two protrusions or jaws 68 and 70 shaped like a pincer or forceps are disposed, which comprise the first electrode 16 or the second electrode 18 on their sides facing the respective other protrusion. The pincer shaped protrusions 68 and 70 can be moved to a closed state from the open state illustrated in FIG. 7a through the actuation lever 64, in which the two pincer shaped protrusions 68 and 70 clamp tissue disposed there between like a pair of pincers. As recited supra, the protrusions 68 and 70 are preferably moved through parallel kinematics, which has the effect that the two electrodes 16 and 18 extend parallel to one another in each open state of the electrosurgical instrument 60, so that the pressure imparted upon the body tissue layers during the tissue fusion is as uniform as possible.

FIG. 7d illustrates how an incision 56 can be treated by means of such an electrosurgical instrument 60 and the material layer 10 according to the invention. The material layer 10 is placed between the body tissue layers to be fused with one another and these are then clamped between the electrodes 16 and 18 disposed at the pincer shaped protrusions 68 and 70. For this purpose, the treating physician has to actuate the actuation lever 64 at the handle 62 of the electrosurgical instrument, and a high frequency AC power is applied to the electrodes 16 and 18 simultaneously through actuating the separate switch or also through actuating the actuation lever 64. For this purpose, the electrodes 16 and 18 are connected through the proximal end of the electrosurgical instrument 60 with a high frequency generator, which is not shown in more detail, like the high frequency generator 28 of FIG. 2.

FIGS. 8a-8d illustrate how electrosurgical instruments 60 similar to the electrosurgical instrument 60 of FIG. 7 with a flexible shaft can be used for treating hollow organs from the inside, in order to perform e.g. a transluminal endoscopic surgery (NOTES). Thus, the flexible shaft of the electrosurgical instrument is inserted e.g. into the operating channel of a hollow shaft 82 of an endoscope 80 so that two pincer type protrusions 68 and 70 of the electrosurgical instrument 60 protrude from the distal end of the hollow shaft 82. Similar to the illustration in FIG. 7, an incision of the hollow organ from the interior of the hollow organ can be treated in that the body tissue layers disposed in the portion of the incision and a material layer according to the invention inserted in between are clamped by the pincer shaped protrusions at the distal end of the electrosurgical instrument and treated electrosurgically thereafter in that the electrodes 16 and 18 introduce high frequency AC power at the pincer shaped protrusions into the body tissue layers to be fused and through the material layer 10 disposed there between.

Figure 9A:
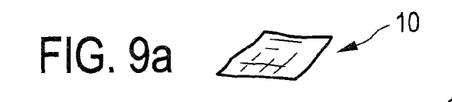
FIGS. 9a-9h illustrate another embodiment of an application.
Figure 9B:
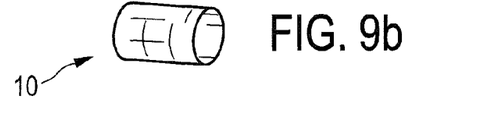

The FIGS. 9a-9h eventually illustrate how two ends of a hollow organ with an instrument similar to the electrosurgical instrument 60 of FIG. 5 can be connected by side to side anastomosis. According to the invention, a material layer 10 is also used for this purpose, which as illustrated in FIG. 9a, can have a flat shape and can also have a shape of the enveloping surface of a cylinder as illustrated in FIG. 9b. For connecting two ends of a hollow organ with one another, so that the hollow organ subsequently has a pass-through lumen, both material layers are required for the method illustrated in FIG. 9 (differently from the method illustrated in FIG. 6), on one side the flat material layer 10 of FIG. 9a and on the other side, the material layer 10 of FIG. 9b shaped as an enveloping surface layer of a cylinder.

Figure 9C:
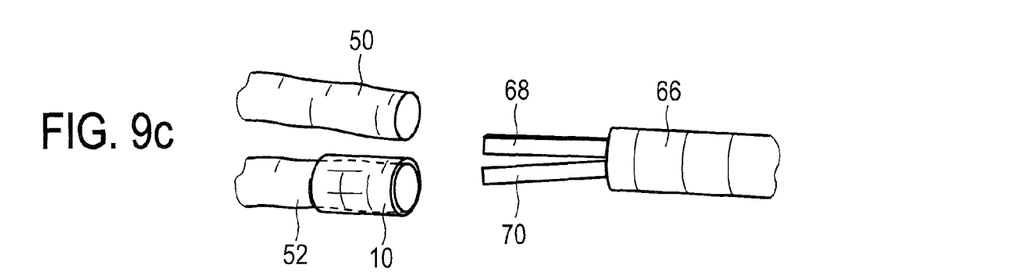
Figure 9D:
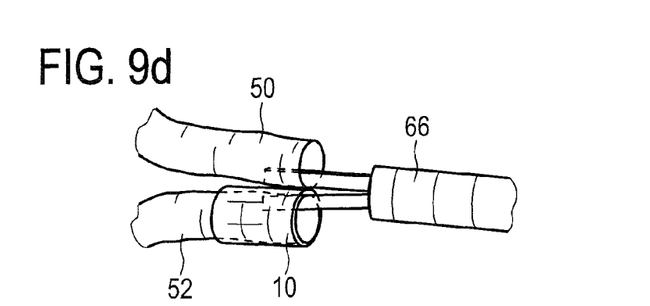

As illustrated in FIG. 9c, a material layer 10 shaped as an enveloping surface layer of a cylinder is initially slid over one of the ends of a hollow organ to be connected with one another, e.g. of an intestine, as it is also illustrated in FIG. 9b. Subsequently, from the two pincer shaped protrusions at the distal end of the electrosurgical instrument, one respective protrusion is inserted into the open end of the hollow organ and the respective other protrusion is inserted into the other end of the hollow organ. Subsequently, the two pincer shaped protrusions 68 and 70 are moved towards one another, so that they respectively enclose one wall section of the ends of the hollow organ to be connected with the material layer disposed there between. This is illustrated in FIG. 9d. In this state, a high frequency AC power current can be conducted through the respective body tissue layers in order to cause fusion in this manner.

Figure 9E:
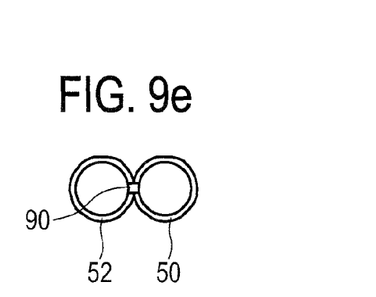

Thereafter, the wall sections thus welded together of the hollow organ to be connected are separated in longitudinal direction, but not quite as far as the respective body tissue layers are fused together. This creates an opening 90 between the laterally welded but still open ends of the hollow organ. This is illustrated in FIG. 9e.

Figure 9F:
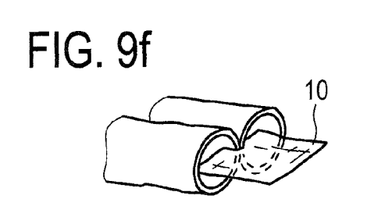

Subsequently, the flat material layer 10 illustrated in FIG. 9a is inserted into the opening 90, but not quite as far as the depth of the incision previously fabricated. This is illustrated in FIG. 9f.

Figure 9G:
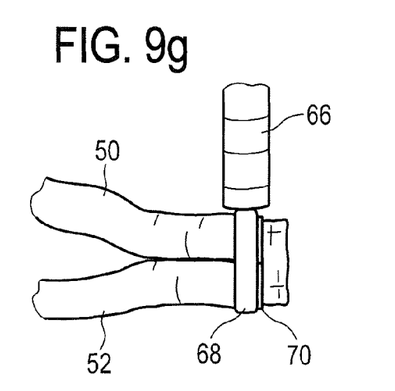
Figure 9H:
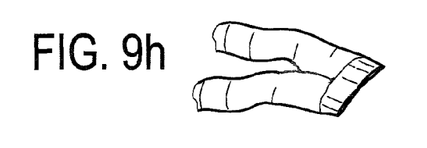

Eventually, the pincer shaped protrusions of the electrosurgical instrument are applied, so that they grip the open ends of the hollow organ transversally from the outside and clamp it between one another. Through the material layer 10, previously inserted, the initially open ends can be fused together as illustrated in FIG. 9g. This closes the fused hollow organ. Between the two fused ends of the hollow organ, however, there is a connection due to the cut (re. FIG. 9e) previously imparted.

Figure 10A:
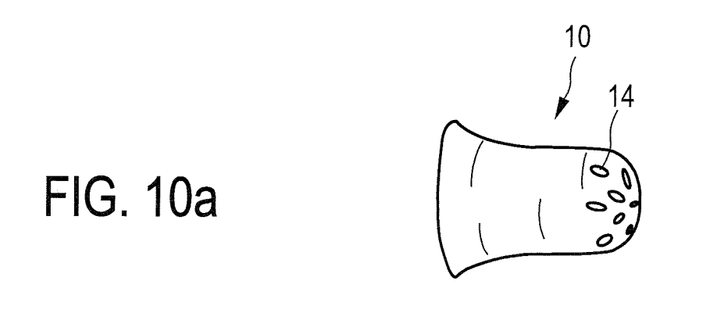
FIGS. 10a-10c illustrate various embodiments of a material layer according to the invention.
Figure 10B:
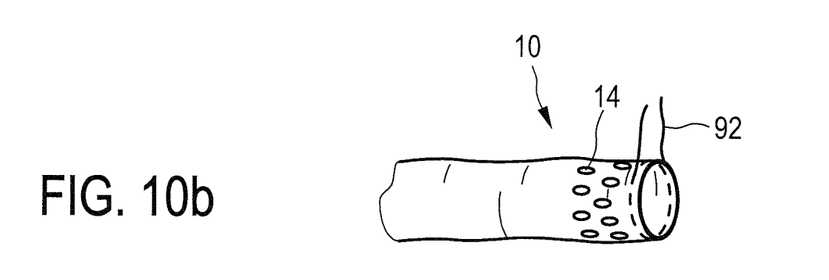
Figure 10C:
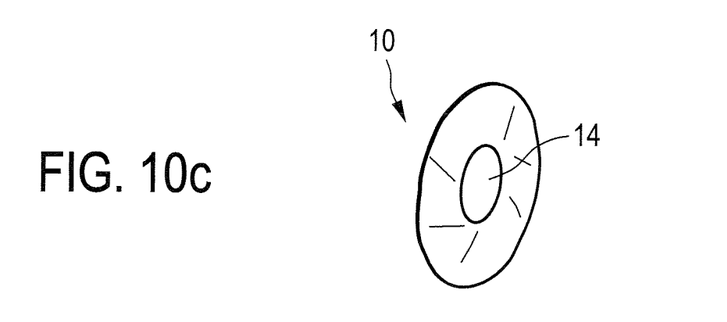

FIGS. 10a, b, c illustrate various embodiments of a material layer 10 according to the invention. FIG. 10a illustrates a material layer 10 in the form of a hose; it has a closed end on the right side in FIG. 10a with a plurality of portions 14. The hose is open on the left end in the depiction and expands towards this end in order to facilitate a better foldover.

FIG. 10b illustrates a material layer 10 shaped as a section of an enveloping surface of a cylinder. It is peculiar for the material layer 10 of FIG. 10b that a purse-string suture with a thread 92 is provided at its right end in the depiction, through which seam the end can be reefed. This is advantageous e.g. in the embodiment illustrated in FIG. 6.

FIG. 10c eventually illustrates a material layer 10 in the form of a circular disc with a central opening, which simultaneously creates a portion 14, which causes low resistance. Additional lower surface area portions 14 can also be provided. By the same token, instead of the large central opening, no opening can be provided but only a plurality of portions 14.

The invention claimed is:

1. A method of fusing layers of biological tissue by connecting two open ends of a hollow organ through side to side anastomosis through tissue fusion such that the hollow organ has a pass-through lumen, the method comprising steps of:
providing a bipolar electrosurgical instrument having two electrodes, a shaft, and two pincer shaped protrusions with the two electrodes attached thereto and arranged on a distal end of the shaft, the protrusions being movable from an open state to a closed state;
providing a first, flat biocompatible material layer and a second biocompatible material layer having a shape of an enveloping surface of a cylinder, each of the first and second material layers having two sides that are opposite to one another, connected to each other, and electrically conductive, and each of the material layers comprising portions with comparatively higher electrical resistance and portions with comparatively lower electrical resistance, the portions with comparatively lower electrical resistance comprising an air gap;
sliding the second material layer over one of the ends of the hollow organ to be connected;
inserting one protrusion of the two pincer shaped protrusions of the electrosurgical instrument into one open end of the hollow organ and the other protrusion of the electrosurgical instrument into the other open end of the hollow organ;
moving the two protrusions to their closed state so that they enclose a wall section of each of the ends of the hollow organ to be connected to the second material layer disposed therebetween;
applying a high frequency AC power to the electrodes of the electrosurgical instrument, thereby providing a variable electrical current flow through the wall sections and thus fusing the wall sections with one another through thermal energy;
creating an opening between the laterally welded but still open ends of the hollow organ;
inserting the first material layer into the opening;
applying the pincer shaped protrusions such that they grip the open ends of the hollow organ transversally from the outside and clamp them between one another; and
fusing together the initially open ends, thereby closing the fused hollow organ.

* * * * *